United States Patent [19]
Spillman, Jr.

[11] Patent Number: 5,600,133
[45] Date of Patent: Feb. 4, 1997

[54] STRUCTURAL ANALYZER USING ACOUSTO-OPTIC SENSOR

[75] Inventor: William B. Spillman, Jr., Charlotte, Vt.

[73] Assignee: Simmonds Precision Products, Inc., Akron, Ohio

[21] Appl. No.: 431,484

[22] Filed: May 1, 1995

Related U.S. Application Data

[63] Continuation of Ser. No. 34,994, Mar. 22, 1993, abandoned.

[51] Int. Cl.$^6$ ............................................. G01N 29/04
[52] U.S. Cl. .................... 250/227.14; 73/606; 73/646; 73/655
[58] Field of Search ............... 250/227.14, 227.16, 250/227.21; 385/12, 13; 367/140; 73/624, 655, 600, 644, 627, 606, 607, 603, 598, 632, 656, 657, 696, 643, 645, 646

[56] References Cited

U.S. PATENT DOCUMENTS

| | | | |
|---|---|---|---|
| 3,910,105 | 10/1975 | Hoffstedt | 73/800 |
| 4,162,397 | 7/1979 | Bucaro et al. | 250/227.14 X |
| 4,265,122 | 5/1981 | Cook et al. | 73/627 |
| 4,312,562 | 1/1982 | Segawa et al. | 385/40 |
| 4,375,680 | 3/1983 | Cahill et al. | 356/345 |
| 4,388,832 | 6/1983 | Kaule | 356/358 |
| 4,481,821 | 11/1984 | Chamuel | 73/617 |
| 4,603,584 | 8/1986 | Bartle et al. | 73/602 |
| 4,654,520 | 3/1987 | Griffiths | 250/227.14 |
| 4,669,814 | 6/1987 | Dyott | 385/42 |
| 4,788,868 | 12/1988 | Wilk | 73/760 |
| 4,840,481 | 6/1989 | Spillman | 356/32 |
| 4,863,270 | 9/1989 | Spillman | 356/345 |
| 4,952,797 | 8/1990 | Spillman, Jr. | 250/227.21 |
| 4,970,467 | 11/1990 | Barnett | 324/637 |
| 5,297,436 | 3/1994 | Chan et al. | 73/657 |

OTHER PUBLICATIONS

Krautkrämer et al., *Ultrasonic Testing of Materials*, 3rd ed., 1983, pp. 174–559.

*Primary Examiner*—Edward P. Westin
*Assistant Examiner*—John R. Lee
*Attorney, Agent, or Firm*—Leonard L. Lewis; Richard A. Romanchik

[57] ABSTRACT

An acousto-optic damage detector and locator uses acoustic energy propagated through a structure to modulate light transmitted through an optical fiber whereby the character of acoustic signals detected by the fiber varies according to the physical condition of the portion of the structure through which the pulses propagate to determine the existence, location and extent of faults within the structure.

17 Claims, 2 Drawing Sheets

STRUCTURAL ANALYZER USING ACOUSTO-OPTIC SENSOR

This is a continuation of application Ser. No. 08/034,994 filed on Mar. 22, 1993, now abandoned.

BACKGROUND OF THE INVENTION

The invention relates to apparatus and methods for structural analysis. More specifically, the invention relates to structural analysis using optics. Internal and surface condition monitoring of structures, such as composite structures used in advanced aircraft, for signs of stress, strain, shear, delamination and other structural failure as well as to verify structural integrity is an important function in structural analysis and preventative maintenance. Optical fiber has heretofore been used within structures to sense physical changes which affect propagation of light through the fiber such as disclosed in U.S. Pat. No. 4,863,270. Such systems typically require expensive electronic processing of the light output of the fiber to convert detected wavelengths, as compared to input light, to analog values. The cost and complexity of such systems prohibits extensive application throughout large structures such as commercial aircraft. The accurate function of such fiber optic sensors is also heavily dependent upon the processing electronics.

SUMMARY OF THE INVENTION

The present invention overcomes these and other disadvantages of the prior art by providing an active acousto-optic sensor which uses optic fiber technology to detect acoustic energy propagating through a structure to be analyzed.

In accordance with one aspect of the invention, a structure analyzing sensor is provided which includes means for sending acoustic signals through a structure and means within the structure for optically sensing the acoustic signals.

In accordance with another aspect of the invention, a structure analyzer is provided which includes means for producing and sending an acoustic signal through a structure to be analyzed, means for modulating light from a light source in response to the acoustic signal, and means for detecting the modulated light.

In accordance with another aspect of the invention, a structure analyzing device is provided which includes an acoustic pulse generator for directing acoustic pulses into a structure to be analyzed, an optical fiber embedded in the structure to be analyzed so that the acoustic pulses intersect the fiber, a light source directed through the fiber, and means for detecting light output by the fiber when a portion of the fiber is intersected by the acoustic pulses.

In accordance with another aspect of the invention, a method of analyzing the condition of a structure is provided which includes the steps of sending an acoustic signal through the structure to be analyzed, and modulating light in response to the acoustic signal.

In accordance with another aspect of the invention, a method is provided for detecting faults in a structure including the steps of embedding at least one optical fiber in the structure, inputting light through the fiber, sending acoustic pulses through the structure whereby the pulses intersect the embedded fiber and detecting light output by the fiber at least a portion of which has been intersected by the pulses to determine faults within the structure.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

DETAILED DESCRIPTION OF PREFERRED EMBODIMENTS

Acoustic energy consists of moving waves which can physically modulate light within an optical fiber upon impact of acoustic wave fronts with the fiber which alters the internal transmission (e.g. diffraction) of light passing through the fiber. By attaching or embedding optical fibers within a structure through which acoustic energy is propagated, faults in the interior of the structure can be detected.

Figure 1:
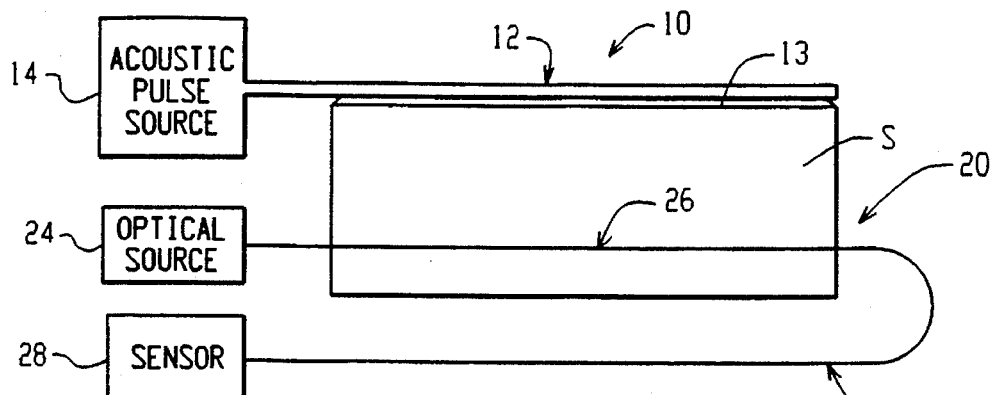
FIG. 1 schematically illustrates an active acousto-optical detector as applied to a structure in accordance with the present invention.

FIG. 1 illustrates an active acousto-optic detector, indicated generally at 10, as applied to a structure S. The structure S may be, for example, a composite structural member. Carbon composite materials, for example, are used for aircraft structures like air foils, leading edges, wings and so forth. Such materials are particularly suitable for use with the invention because they exhibit good acoustic coupling characteristics. However, this is but one of many examples of materials and/or structures which the invention can be used with, and should not be construed in a limiting sense. Those skilled in the art will readily appreciate that the invention can be used with any structure and material that can be characterized with acoustic signatures. The detector 10 includes an acoustic transmitter, indicated generally at 12, attached or integrated into a surface 13 of structure S. The acoustic transmitter 12 may be, for example, a "lossy" wave guide, such as a rectangular strip wave guide as is well known to those skilled in the art. Such a wave guide allows a sufficient amount of acoustic energy, input to the transmitter 12 by an acoustic pulse source 14, to leak from the wave guide into and through the structure S. The acoustic transmitter 12 may be of any configuration and orientation to send acoustic pulses through structure S in any desired pattern and may also be incorporated into the body of structure S. The acoustic pulse source 14 may be any commercially available acoustic pulse generator.

With continuing reference to FIG. 1, an optical sensor, indicated generally at 20, is shown integrated with structure S. The optical sensor 20 includes an optical fiber 22 connected to an optical source 24. The optical fiber 22 may be any commercially available fiber of suitable gauge such as single mode or multimode fiber. The optical source 24 may provide any suitable spectrum of light and/or simply provide broad band light. A portion 26 of the optical fiber 22 is embedded or otherwise attached to structure S in a predetermined relationship with respect to the acoustic transmitter 12 to achieve a predetermined and preferably optimized acousto-optic coupling. Acousto-optic coupling as used herein refers to any physical change or modulation of an optical signal by an acoustic signal such that the optical signal is modulated in response to the acoustic signal. For example, embedded fiber portion 26 may be arranged parallel to acoustic transmitter 12 to achieve maximum detection of each acoustic pulse as it dissipates along acoustic transmitter 12 and propagates through structure S. The remaining portion of optical fiber 22 leads to an output sensor/processor 28 which detects the modulated optical signal in the form of a characteristic signature which corresponds to the acoustic energy affecting the embedded fiber portion 26 of optical fiber 22.

The operation of the acousto-optic detector in accordance with the invention is now described with reference to FIGS. 1 and 2. An acoustic signal from source 14 is directed to propagate through and along the length of the acoustic transmitter 12. As an acoustic pulse travels along the length of transmitter 12, a portion of the acoustic energy of the pulse is leaked or propagates into structure S in the direction of embedded fiber portion 26 of optical fiber 22. The acoustic energy of each pulse leaked from transmitter 12 impacts upon embedded fiber portion 26 of optical fiber 22. The acoustic energy causes the fiber to vibrate, bend, compress or otherwise exhibit a physical response so as to change the amount and/or pattern of light which passes through the fiber from light source 24 to fiber output sensor/processor 28. Preferably, an interference pattern of the light from the fiber is detected. The sensor/processor 28 produces an output that can be read in analog or digital form to represent a characteristic signature of the portion of the structure through which the pulse has traveled.

Alternatively, the output of embedded fiber portion 26 can be read directly as an active sensor by use of, for example, a sensor 28 in the form of an interferometer such as a Mach-Zehnder interferometer, diffraction gratings, or modal interference. For example, the processor 28 could be used to detect an intermodal speckle pattern that changes in response to the acoustic energy imparting the fiber. The speckle pattern can be detected by convening variation is a function of the acoustic signature which depends on the acoustic energy dissipation through the structure, as well as structural defects and characteristics that affect the acoustic energy transmission. Of course, other interference patterns can conveniently be used to detect the acoustic signature.

Figure 2:
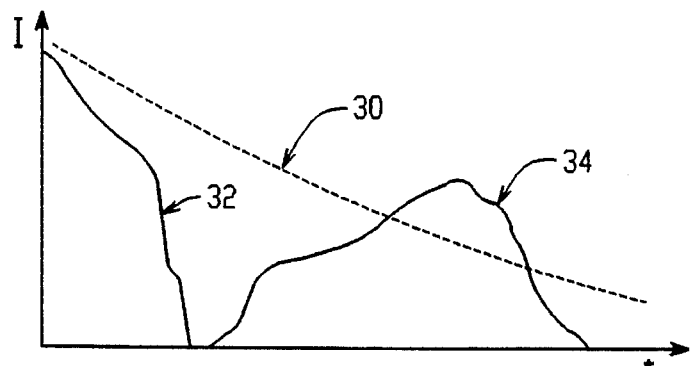
FIG. 2 is an X-Y representative graph of acoustic signatures detected by an active acousto-optic detector in accordance with the present invention.

Line 30 of the plot of FIG. 2 represents a detected signature versus time corresponding to a signature produced by an ideal structure, i.e., complete absence of faults such as cracks, delamination or stress, resulting in a smooth slope of the detected signal. For example, the optical energy received from the fiber 22 by the processor 28 can be convened to a current, I, by a photodetector. The declining slope of the detected signature represents dissipation of acoustic energy of the pulse through the interior of the structure as it travels along and leaks from acoustic transmitter 12. Line 32 in FIG. 2 represents a deviation of the detected signature from the normal sloping dissipation of acoustic energy as a result of the presence of a physical interference or obstruction to propagation of the acoustic pulse through the structure. For example, a complete delamination or void within the structure sufficient to attenuate propagation of an acoustic wave can result in reduced or no detection by the embedded fiber portion 26 of optical fiber 22 of acoustic energy. Conversely, as represented by line 34, an area of concentrated stress or strain forces within the structure can act as an acoustic lens to magnify the force of the acoustic pulse upon the fiber causing an identifiable deviation, in this case an apparent magnification type deviation, from the ideal structure signal curve 30.

The light signal from the optical fiber can also be analyzed to determine at what point along the energy dissipation path such deviations have occurred, and these points then correlated to physical locations within the structure. For example, by timing the rate of propagation of each acoustic pulse through the structure, an alteration in the modulated light pattern indicates a linear position of a structural defect between the acoustic wave guide and the sensing fiber. Similarly, the magnitude of the deviations from the known signature can be correlated to the dimensional magnitude of the causal fault within the structure.

Figure 3:
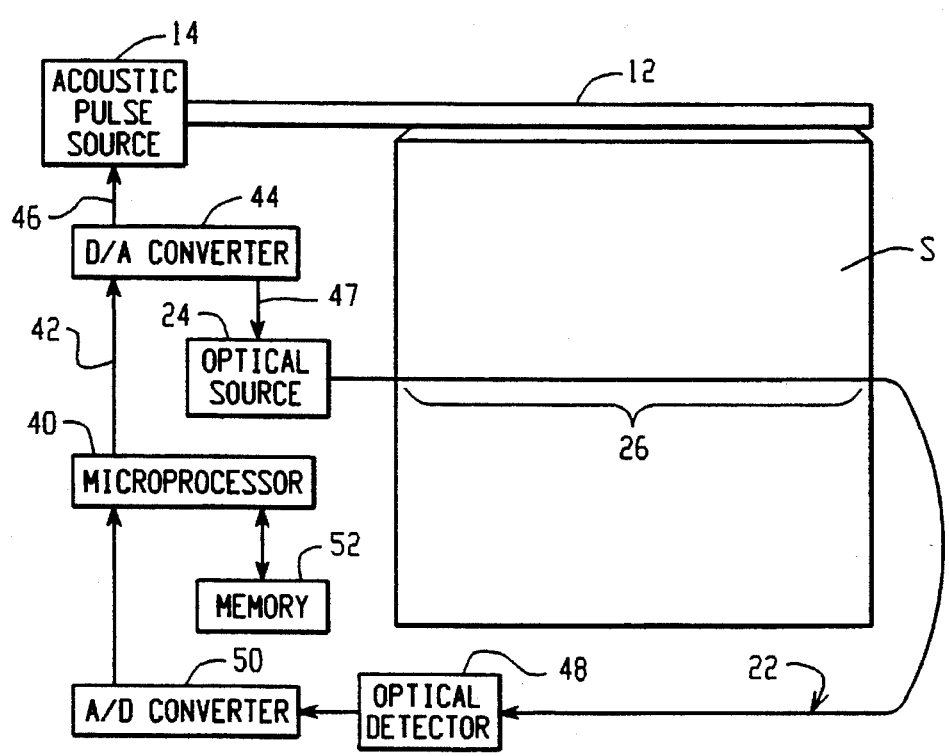
FIG. 3 illustrates a detailed schematic of an active acousto-optical detector as applied to a structure in accordance with the present invention.
Figure 4:
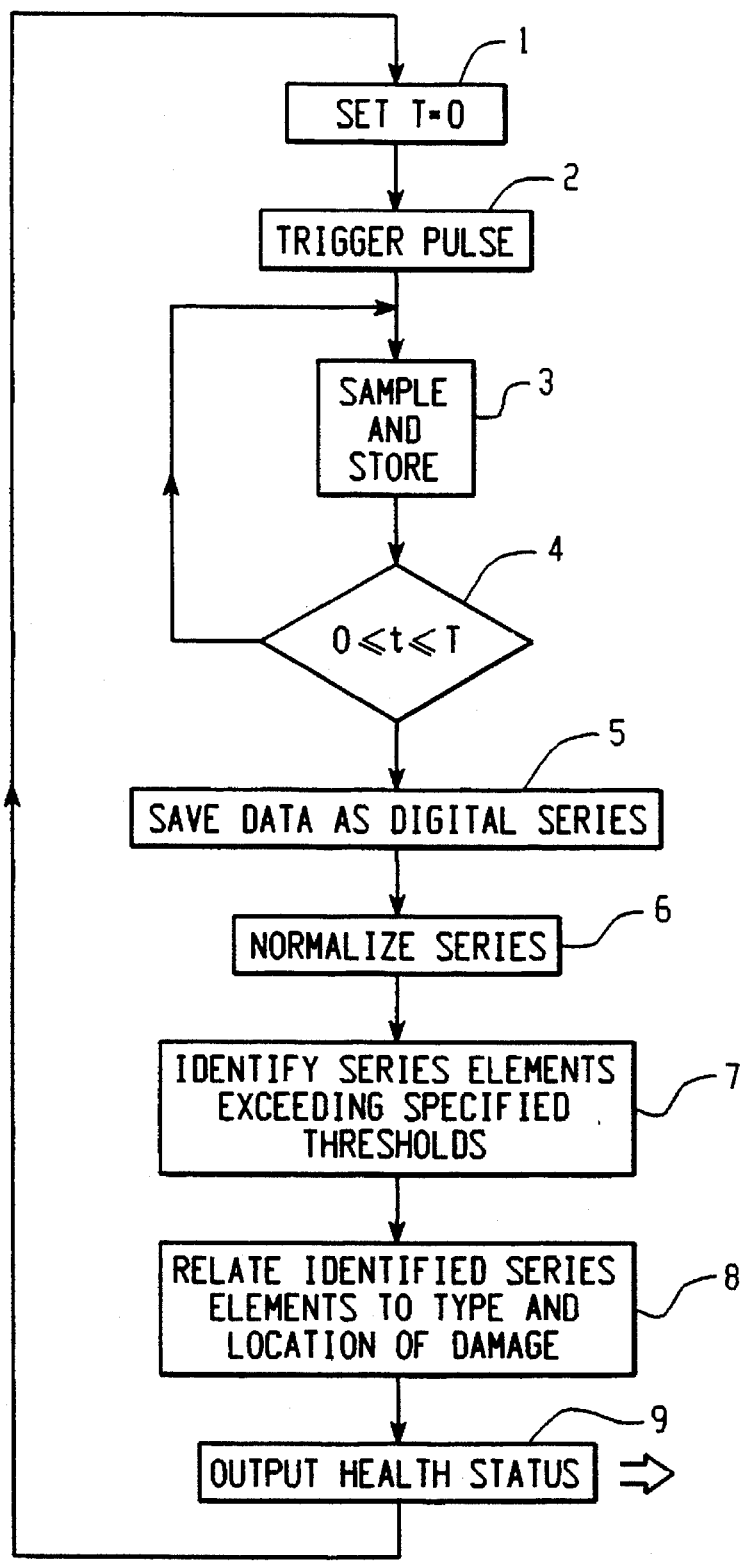
FIG. 4 is a flow chart of the operation of the acousto-optical detector of FIG. 3.

With reference to FIGS. 3 and 4, a more detailed description of the operation of the preferred embodiment of an active acousto-optic detector 10 is given. At the beginning of each measurement cycle, a microprocessor 40 initiates a digital timing pulse which is sent via line 42 to a digital to analog (D/A) converter 44. The D/A converter 44 produces an analog electrical pulse which is transmitted via line 46 to acoustic pulse source 14. The D/A converter 44 also sends an analog signal to optical source 24 via line 47 to initiate an optical signal of suitable wavelengths or broad band light transmitted through fiber 22. Acoustic pulse source 14 then generates a short acoustic pulse into the coupled acoustic transmitter 12. As the acoustic pulse travels the length of acoustic transmitter 12, a portion of the acoustic energy is leaked into the structure S and passes through it and impinges upon the embedded fiber portion 26 of optical fiber 22.

During the time period in which the acoustic pulse is traveling along the acoustic transmitter 12, e.g., a total time T, a characteristic response is obtained from changes in the detected optical signal, induced by the energy of the acoustic pulse which impinges upon embedded fiber portion 26, by optical detector 48. The analog optical signals detected by optical detector 48 are converted into digital electrical signals by A/D converter 50. Digitized signals from A/D converter 50 are then transmitted to microprocessor 40 and stored in memory 52.

An exemplary data processing sequence of the detector 10 is represented by the succession of boxes 1–9 of the flow chart of FIG. 4 for a time T after an acoustic pulse is sent. The entire response is saved as a digital series in the memory 52. Steps 1–5 represent transmission of an acoustic pulse and receipt and storage in memory of the optically detected and digitized series of signals during the time period T. A reference digital series of a response of an undamaged structure, obtained either analytically or empirically, may also be stored in the memory 52. At step 6, microprocessor 40 divides (normalizes) the detected data series by the stored reference series. At steps 7–9, the elements of the normalized series are analyzed by microprocessor 40 to see whether they exhibit criteria which indicate specific damage conditions. For example, the position of a piece of digital data in a series relates to a specific region of the structure while its magnitude, sign, and derivative relate to the condition of the structure. Structural condition verses location is then produced as output of the microprocessor 40 and the process repeated. The circuit of FIG. 3 and sequence of FIG. 4 is only intended to be representative of an apparatus for processing the acousto-optic detector 10 output. All of the components are conventional and well known to those skilled in the art. Other circuits can suitably be used to realize the advantages of the present invention.

Although the invention has been shown and described with respect to a preferred embodiment, it is obvious that equivalent alterations and modifications will occur to others skilled in the art upon the reading and understanding of this specification. The present invention includes all such equivalent alterations and modifications, and is limited only by the scope of the claims.

What is claimed is:

1. An acousto-optic structure analyzer comprising, means for transmitting acoustic energy through an elongated acoustic wave guide that is acoustically coupled along its length to the structure so that acoustic energy is transmitted through at least a corresponding portion of the structure along the length of said wave guide to produce a transmissive acoustic signature distributed over said length, and means for modulating light in response to said acoustic energy to produce a light pattern representative of said distributed acoustic signature.

2. The analyzer of claim 1 wherein said wave guide is embedded within said structure.

3. The analyzer of claim 1 wherein said means for modulating light in response to said acoustic signature comprises an optical fiber.

4. The analyzer of claim 3 wherein said optical fiber is physically coupled to said structure.

5. The analyzer of claim 3 wherein a portion of said optical fiber is within said structure.

6. The analyzer of claim 1 further comprising means for detecting light modulated in response to said acoustic signature.

7. The analyzer of claim 6 wherein said means for detecting light comprises means for detecting the intensity of said light.

8. The analyzer of claim 6 wherein said means for detecting light comprises an interferometer.

9. The analyzer of claim 6 wherein said means for detecting light comprises a diffraction grating.

10. The analyzer of claim 1 wherein said modulating light means comprises an optic fiber that coextends along the structure with said wave guide means to detect said transmitted acoustic energy distributed through the structure along the length of said wave guide.

11. The analyzer of claim 10 wherein acoustic energy is distributed through said corresponding structure portion along said wave guide length by leaking from said wave guide into the structure along said wave guide length acoustically attached to the structure.

12. The analyzer of claim 11 wherein said wave guide is embedded in the structure.

13. The analyzer of claim 11 wherein said optic fiber is embedded in the structure.

14. The analyzer of claim 1 further comprising an acoustic energy source that transmits acoustic energy into said wave guide, said acoustic energy propagating along said wave guide means for a determinable time period T such that acoustic energy distributively leaks into the structure towards said light modulating means along said length of the wave guide, so that modulated light signals detected during said period T represent an acoustic signature of the structure along a distributed portion of the structure.

15. The analyzer of claim 14 further comprising means for detecting said light pattern and producing first signals representative thereof during at least the time period T, and means for comparing said first signals with corresponding second signals representative of a reference pattern.

16. A method for analyzing a structure comprising the steps of, providing an elongated acoustic wave guide acoustically coupled along its length to the structure;

transmitting acoustic energy along the length of the wave guide into a corresponding portion of the structure to be analyzed to produce a distributed transmissive acoustic signature, and modulating light in response to said distributed acoustic signature to produce a light pattern that represents said signature.

17. The method of claim 16 further including the step of detecting said light modulated in response to said acoustic signature.

* * * * *